United States Patent

Wilson et al.

(10) Patent No.: US 8,308,781 B2
(45) Date of Patent: Nov. 13, 2012

(54) MULTIPLE LUMEN SENSOR ATTACHMENT (75) Inventors: Stephen F. Wilson, North Easton, MA (US); Michael C. Gorhan, Mansfield, MA (US)

(73) Assignee: Codman & Shurtleff, Inc., Raynham, MA (US)

( * ) Notice: Subject to any disclaimer, the term of this patent is extended or adjusted under 35 U.S.C. 154(b) by 458 days.

(21) Appl. No.: 12/556,035

(22) Filed: Sep. 9, 2009

(65) Prior Publication Data
US 2009/0326519 A1  Dec. 31, 2009

Related U.S. Application Data (62) Division of application No. 10/839,952, filed on May 4, 2004, now Pat. No. 7,604,658.

(51) Int. Cl.
*A61B 17/04* (2006.01)
*A61B 17/86* (2006.01)
*A61F 2/08* (2006.01)

(52) U.S. Cl. ........................................... 606/304
(58) Field of Classification Search .................. 606/72, 606/73, 108, 301–321
See application file for complete search history.

(56) References Cited

U.S. PATENT DOCUMENTS

| 3,055,370 A | * | 9/1962 | Mckinney et al. | 606/129 |
| 5,842,865 A | * | 12/1998 | Bassett et al. | 433/174 |
| 6,454,774 B1 | * | 9/2002 | Fleckenstein | 606/108 |

FOREIGN PATENT DOCUMENTS
WO    WO 02/070037 A2    9/2002

OTHER PUBLICATIONS
JP Application No. 2005-134371; Office Action dated Nov. 30, 2010.

* cited by examiner

*Primary Examiner* — Kevin T Truong
*Assistant Examiner* — Sameh Boles (57) ABSTRACT

A cranial bolt secured to a skull of a patient includes a threaded portion and a lumen portion. Threaded portion has an inner surface forming a central passageway which extends throughout the threaded portion. The inner surface includes a connector mating with the lumen portion. The lumen portion includes a stem portion that enters the central passageway and engages the mating connector. A fluid tight seal is formed between the inner surface of the threaded portion and the stem portion. At least two lumens are disposed through the stem portion and the base portion. The lumens have a proximal end opening outside the skull and a distal end opening inside the skull. One embodiment includes sensor lumens diverging from the centerline and another allows the lumen portion to rotate independent of the threaded portion.

7 Claims, 8 Drawing Sheets

MULTIPLE LUMEN SENSOR ATTACHMENT

CROSS REFERENCE TO RELATED APPLICATION

The present application is a divisional of U.S. patent Ser. No. 10/839,952, filed May 4, 2004.

BACKGROUND OF THE INVENTION

1. Field of the Invention

This invention relates to a two piece cranial bolt having a threaded portion to engage the skull and a lumen portion to engage the threaded portion.

2. Discussion of the Related Art

For certain medical conditions, such as head trauma, it is necessary to place sensors into the brain of the patient. Many of the prior art devices are designed to penetrate the skull, and be fixed in place to allow for the passage of a sensor probe or catheter to the brain. However, most prior art bolts have one opening that allows for only one probe or catheter to reach the brain through the skull. The prior art devices do not allow for multiple readings at the same location or do not allow for a reading or multiple readings to be taken along with the placement of a catheter to drain pressure building up inside the cranium. These prior art devices require the drilling of multiple holes in a patient's skull or the necessary probes and catheters must be removed and replaced as readings or drainage is required.

U.S. Pat. No. 3,055,370 to McKinney et al. ("McKinney") discloses a tap assembly 10 including a tap 11 and holder 12. A single tubular member 13 extends through both tap 11 and holder 12 to allow needle 34 to pass through. Tubular member 13 can change orientation because it passes through ball 14, located inside tap 11 and under holder 12. Holder 12 is threaded into tap 11 and applies force to ball 14 to lock tubular member 13 at the correct orientation. However, McKinney only allows for one instrument at a time to pass through tubular member 13 and it cannot be converted to allow for multiple passageways because of the design of the locking mechanism using holder 12, i.e. only one passageway can be accommodated per tap assembly because of ball 14. McKinney suggests that tap 11 and holder 12 can be assembled once tap 11 is threaded into the patient's skull. However, undue stress will be applied to the patient's skull if tap assembly 10 is assembled after tap 11 is seated in the skull. A particular amount of force is required to assure that ball 14, and thus tubular holder 13, does not move once needle 34 is in place. This force causes undue stress on the patient's skull. U.S. Pat. No. 4,903,707 to Kunte et al. ("Kunte") has similar problems to McKinney wherein bolt means 17 is screwed into the patient's skull 15 and catheter 19 is held in place by clamping means 21 which must be screwed down on bolt means 17.

Another example is U.S. Pat. No. 6,356,792 to Errico et al. ("Errico") which discloses a skull mounted electrode lead securing assembly. Cylindrical skull port member 100 is fitted into a burr hole in the patient's skull. Lead locking element 120 is fitted to the inner surface of port member 100 and allows a single electrical lead to pass through an axial channel 126. However, the crucial element of Errico's invention is lead locking element 130, 132. Sliding element 132 is designed to partially occlude axial channel 126 to prevent the movement of the lead. Errico's invention is not suited for multiple passageways because the locking mechanism requires too much space on the surface of the lead locking element to allow for other passageways on the same lead locking element. Additionally, one skilled in the art would not insert multiple electrodes in Errico's lead locking element because these electrodes would be too close to each other, thereby resulting in inaccurate measurements.

An example of a cranial bolt having multiple channels is illustrated in Great Britain U.S. Pat. No. 2,300,080 to Hutchinson. Hutchinson discloses a single bolt 2 containing a plurality of channels 4 through which instruments may pass to reach the brain. However, Hutchinson's channels 4 converge toward the centerline c of bolt 2 and any instruments passed through these channels will intersect each other a very short distance from inner end 12. The intersection of the multiple instruments poses a problem because every probe that is introduced into the brain tissue causes a certain amount of trauma. Thus, another probe or catheter placed next to a first probe will disturb the readings of the first probe. The first probe will record readings stemming from the trauma and not the actual readings of the patient's brain.

Thus, there is a need in the art for a two piece multiple passageway cranial bolt where each of the implements passed toward the brain diverge in directions toward different areas of the brain to allow for accurate readings of the patient's brain.

SUMMARY OF INVENTION

A cranial bolt to be secured to a skull of a patient includes a threaded portion and a lumen portion. The threaded portion has an inner surface forming a central passageway which extends throughout the threaded portion. The inner surface includes a connector mating with the lumen portion. The threaded portion has an outer surface with a plurality of threads for engaging a hole formed in the patient's skull. Typically, the hole is drilled into a patient's skull using a burr drill and the threaded portion is screwed directly into the hole. Other prior art bolts require the additional step of tapping or threading the hole to provide threads in the skull so the prior art bolt can engage the skull. The threaded portion of the present invention, however, is self-tapping, so it does not require the additional step of tapping the burr hole.

The lumen portion includes a stem portion that enters the central passageway and engages the mating connector. The mating connector can be threads, a friction fit plug, a combination of threads and a plug, a bayonet lock, or any other connector known to those of skill in the art. The mating connector can be formed to lock the lumen portion in place so that once it is engaged with the threaded portion, the two portions cannot be separated. However, a preferred embodiment allows the lumen portion to engage with and disengage from the threaded portion. Different configurations of the lumen portions utilize the same threaded portion. This embodiment reduces the number of burr holes to be drilled into a patient's skull or the number of bolts to be screwed into and out of the same burr hole.

Regardless of the type of mating connector, a fluid tight seal is formed between the inner surface of the threaded portion and the stem portion. In one embodiment the fluid tight seal is formed by an o-ring.

A base portion is disposed on one end of the stem portion opposite the skull. The base portion extends outside and above the threaded portion. At least two lumens are disposed through the stem portion and the base portion. The lumens have a distal end opening inside the skull and a proximal end opening outside the skull. One embodiment has three lumens, a drainage lumen, and two sensor lumens disposed offset from the drainage lumen. Another embodiment includes one or both of the distal ends and/or proximal ends of the lumens diverging at an angle from a centerline of the lumen portion.

A further embodiment includes a drainage lumen disposed along the centerline and the proximal ends of the sensor lumens diverging at the same or different angles from the centerline. Disposing the lumens in a non-coaxial pattern allows the placement of multiple lumens at a distance further from a first lumen while minimizing the size of the bolt. For example, the drainage lumen is typically inserted to drain excess fluid from inside the skull and sensors may be placed through the sensor lumens to take readings of the condition of the brain. However, if the sensors are placed too close to a drainage catheter in the drainage lumen, the sensors will read the stresses and conditions caused by the drainage catheter and not the actual state of the brain. The same condition can occur if the sensors are placed in close proximity to each other.

The cranial bolt can also include a floating collar disposed between the stem portion and the base portion. The floating collar allows the base portion to rotate relative to the stem portion. An additional embodiment allows the lumen portion to rotate relative to the threaded portion. Regardless of embodiment, rotation of the base portion allows for flexible placement of the sensors because the lumens are moved in relation to the rotational placement of the threaded portion in the skull. Prior art bolts either fixed the position of the lumens, once the bolt was screwed to the proper depth, or required the entire bolt to be rotated if the placement of the sensors needed to be changed. The cranial bolt of this embodiment of the invention alleviates the need to move the threaded portion once placed to the proper depth in the skull. The base portion or lumen portion can be rotated independently of the threaded portion to prevent undue stress on the skull.

Different configurations of the lumen portion can be designed for specific purposes. The configurations can vary by numbers of lumens (e.g. 2, 3, or 4), configuration of the lumens (e.g. one central lumen and others offset or all the lumens on the perimeter), and the inclusion of the floating collar.

An embodiment includes a wing engagement portion disposed on a top surface of the threaded portion (the top surface is outside the skull). A wing portion is disposed on an outer surface of the base portion. The wing portion engages the wing engagement portion when the stem portion engages the mating connector. Once engaged, when the base portion is rotated, the threaded portion is rotated along with the base portion. This embodiment permits ease of tightening or loosing of the threaded portion in the skull by rotating just the lumen portion.

An insertion tool can also be provided that engages the threaded portion and provides mechanical advantage to increase the amount of torque applied to the threaded portion while inserting the threaded portion into the skull. The insertion tool further includes an extending arm that extends from the skull. When its work is completed, the insertion tool can be removed from the threaded portion of the cranial bolt.

A method of securing a cranial bolt to a skull of a patient includes drilling a hole in the skull of a patient using a burr and inserting a self-tapping threaded portion of the bolt into the burr hole. A lumen portion is then engaged with the threaded portion and forms a fluid tight seal between an inner surface of threaded portion and a stem part of the lumen portion.

Further methods include removing a first lumen portion from the threaded portion and engaging a second lumen portion. The second lumen portion can have a different configuration than the first lumen. Additional steps include, prior to the inserting step, engaging the threaded portion of the bolt with an insertion tool to increase the torque applied to the threaded portion during the insertion step and, after the inserting step, removing the insertion tool.

BRIEF DESCRIPTION OF THE DRAWING FIGURES

The above and still further objects, features and advantages of the present invention will become apparent upon consideration of the following detailed description of a specific embodiment thereof, especially when taken in conjunction with the accompanying drawings wherein like reference numerals in the various figures are utilized to designate like components, and wherein.

DETAILED DESCRIPTION OF THE PREFERRED EMBODIMENT

Figure 1:
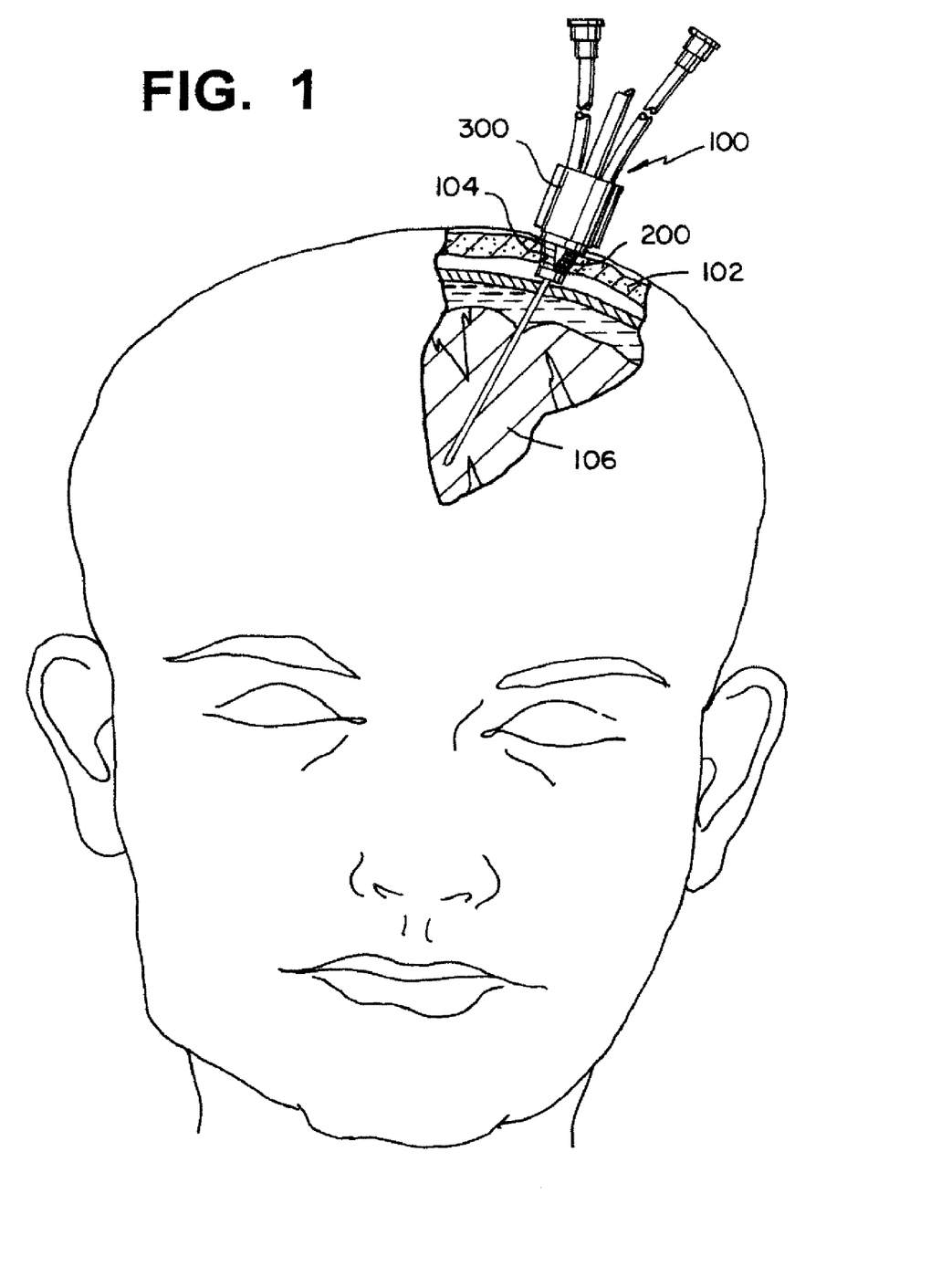
FIG. 1 is an elevation view of the cranial bolt of the present invention installed in a patient's skull.
Figure 3:
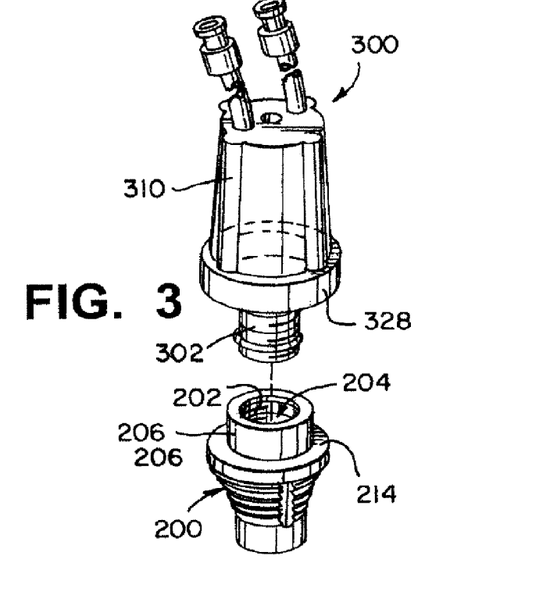
FIG. 3 is an exploded perspective view of a lumen portion and threaded portion of a cranial bolt according to the present invention.
Figures 5, 6:
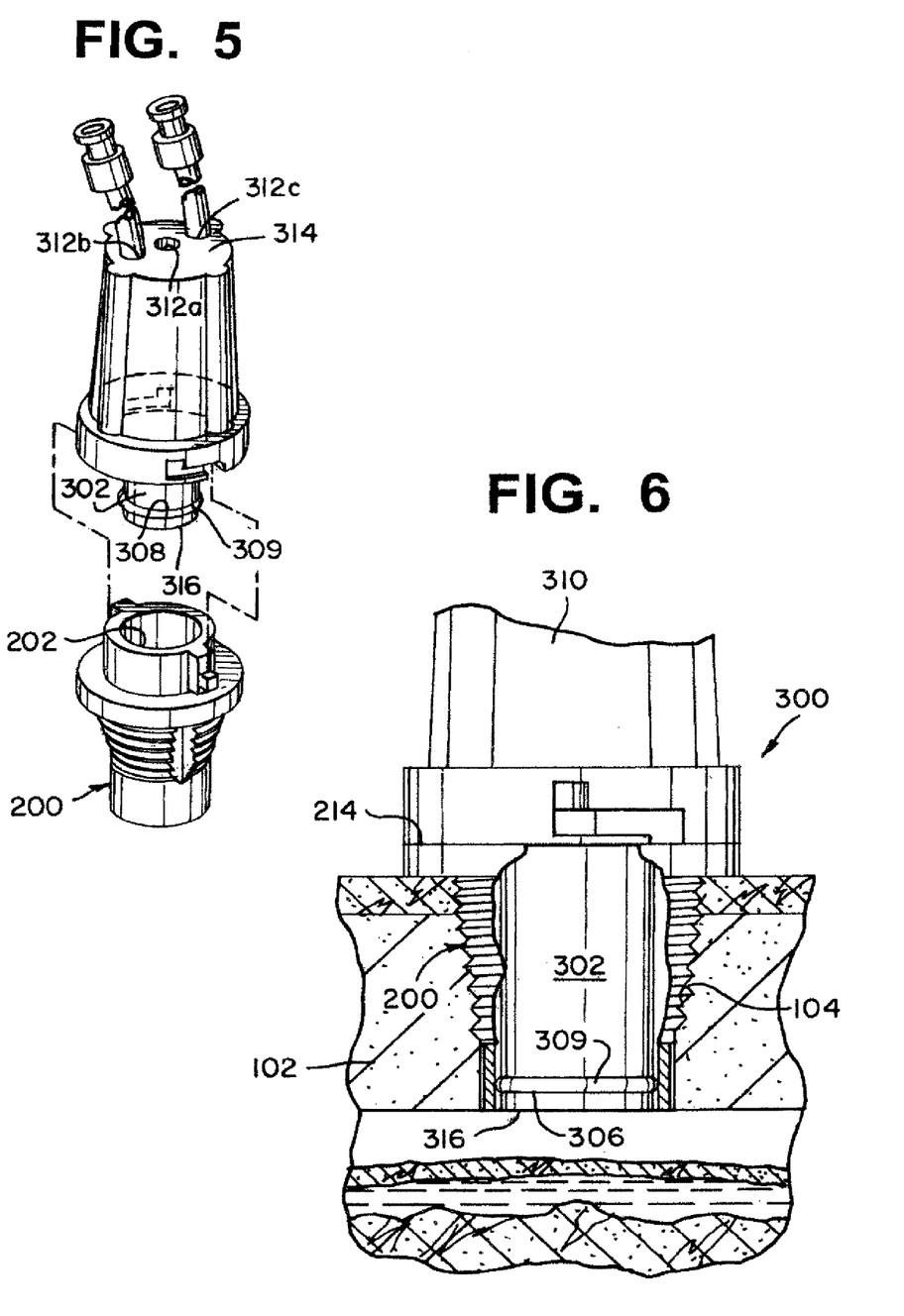
FIG. 5 is an exploded perspective view of another embodiment of the present invention.
FIG. 6 is a cross-sectional view of the lumen portion of FIG. 5 installed in a patient's skull.

Referring to FIG. 1, a cranial bolt 100 according to the present invention is illustrated secured to a skull 102 of a patient. Cranial bolt 100 includes a threaded portion 200 and a lumen portion 300. Threaded portion 200 has an inner surface 202 that forms a central passageway 204 (FIGS. 3 and 6). Central passageway 204 extends throughout the threaded portion 200 and is illustrated having a circular cross section, but can be any geometric shape, e.g. triangle, square, and pentagon (not illustrated). Further, central passageway 204 may not have a uniform diameter throughout its length.

Figure 2:
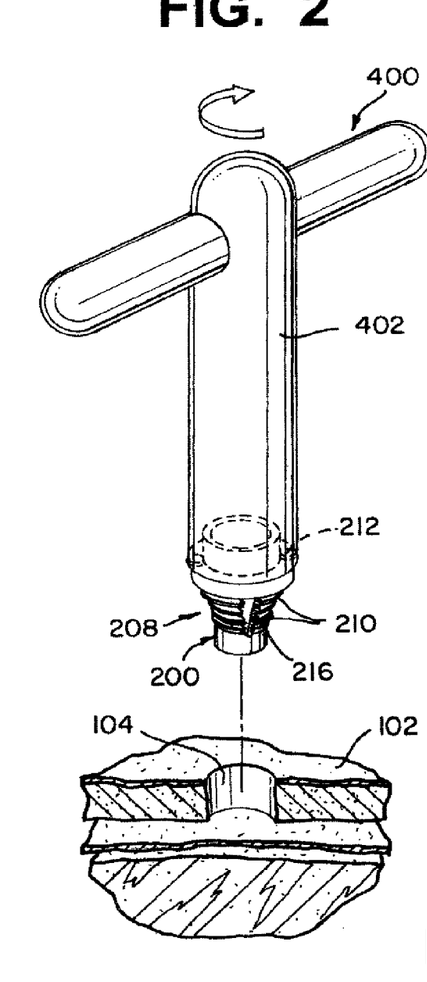
FIG. 2 is a perspective view of an embodiment of the cranial bolt of the present invention engaged by an insertion tool prior to insertion of the bolt into a patient's skull.

Referring now to FIG. 2, threaded portion 200 also has an outer surface 208 with a plurality of threads 210 for engaging a hole 104 formed in skull 102 to fixedly engage threaded portion 200 to skull 102. Typically, a hole is drilled into a patient's skull using a burr drill and, in one embodiment, hole 104 is tapped, or threaded to provide threads for threaded section 200 to engage the skull. In a preferred embodiment, threaded portion 200 and threads 210 are self-tapping and do not require the additional step of tapping hole 104. Self-tapping threaded portion 200 includes a channel or pathway 216 through the threads. Pathway 216 forms a cutting edge where it intersects the threads and a passage for material, i.e. bone, to exit as threaded section 200 is threaded into hole 104. Self-tapping threaded portion 200 reduces the number of steps required and decreases the amount of time required for a given procedure. Threaded portion 200 is made of a material to allow it to self-tap, e.g. metal or hard plastic.

FIG. 2 further illustrates an insertion tool 400 engaging threaded portion 200 by means of recesses in its underside (not shown) that engage projecting or recessed portions 212 in threaded portion 200. Insertion tool 400 provides a gripping surface on an extending arm 402 and mechanical advantage to increase the amount of torque that can be applied to threaded portion 200 while inserting threaded portion 200 into skull 102. In a preferred embodiment, extending arm 402 is "T" shaped and sufficiently long enough to extend from the skull 102 even when threaded portion 200 is fully installed. In another embodiment, insertion tool 400 can also include ridges to facilitate insertion (not illustrated). In this embodiment, insertion tool 400 is removably engaged with threaded portion 200.

Referring to FIG. 3, lumen portion 300 includes a base portion 310 and a stem portion 302 that enters central passageway 204 of threaded portion 200. Threaded portion 200 includes a mating connector 206 that mates with lumen portion 300. Mating connector 206, in a preferred embodiment, can extend past a top surface 214 of the threaded portion 200. Top surface 214 is outside skull 102 when the threaded portion is fully seated. Mating connector 206 engages an inner surface 328 of lumen portion 300. Mating connector 206 can be threads (FIG. 3), a friction fit plug (FIG. 4), a bayonet lock (FIG. 5), a combination of threads and a plug (not illustrated), or any other connector known to those of skill in the art. In another embodiment, mating connector 206 can be disposed on inner surface 202 and can mate with stem portion 302 using the same types of connectors as described and contemplated above.

FIG. 3 illustrates that mating connector 206 can be threads. The threads can be threaded in the same direction as threads 210 or can be threaded opposite, e.g. threads 210 can tighten clockwise and mating threads can tighten counter-clockwise. If threads 210 and mating connector threads 206 are threaded in the same direction, this allows the torque applied to lumen portion 300 to assist in the seating of threaded portion 200 into hole 104. If threads 210 and mating threads 206 are threaded in the opposite direction, this arrangement prevents the torque applied to lumen portion 300 from driving threaded portion 200 deeper in hole 104. Additionally, excess torque applied to lumen portion 300 can assist in removing threaded portion 200 at the end of the procedure.

Figure 4:
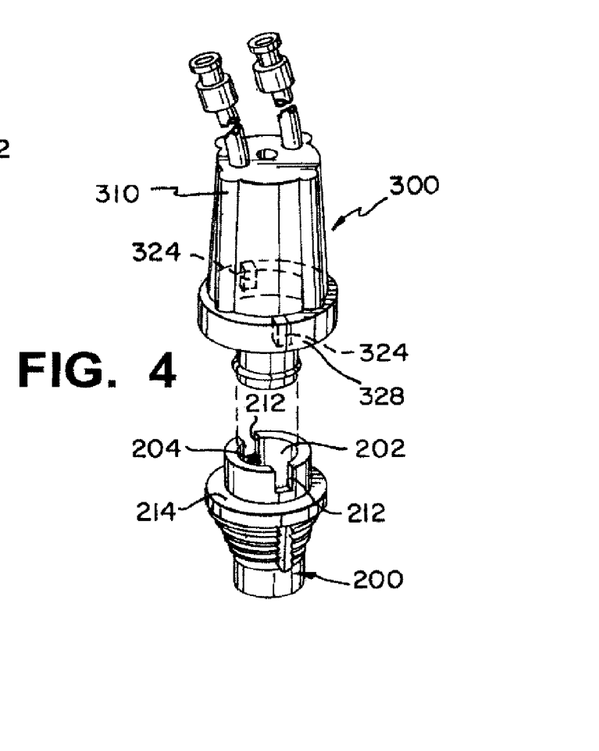
FIG. 4 is an exploded perspective view of another embodiment of the lumen portion of the present invention being inserted into the threaded portion.

FIG. 4 also illustrates an embodiment where wing gaps 212 are disposed on a top surface 214 of threaded portion 200. One or more wing gaps 212 are placed to allow one of lumen portion 300 or a tool, e.g. a flat head screw driver, to engage threaded portion 200 to assist in its placement. A wing portion 324 is disposed on inner surface 328 of the base portion 310. Wing portion 324 engages wing gaps 212 when stem portion 302 engages mating connector 206. Wing gaps 212 can be raised to engage wing portion 324 once stem portion 302 is fully inserted into central passageway 204. Wing gaps 212 can also engage base surface 310. In one embodiment where mating connector's threads 206 are threaded the same as threads 210, the engagement between wing gaps 212 and wing portions 324 can prevent the lumen portion 300 from rotating separately from threaded portion 200. Additionally, once engaged, when base portion 310 is rotated, threaded portion 200 is rotated according to base portion 310. This embodiment permits ease of tightening or loosing of threaded portion 200 to skull 102 by using just lumen portion 300.

Mating connector 206 can be formed to lock lumen portion 300 in place so, once engaged with threaded portion 200, the two portions cannot be separated. However, as illustrated in FIGS. 4, 5 and 6, preferred embodiments allow lumen portion 300 to be engaged and disengaged from threaded portion 200. FIG. 4 illustrates a friction fit mating between threaded section 200 and lumen section 300. Further, FIGS. 5 and 6 illustrate a bayonet lock to engage lumen portion 300 to threaded portion 200.

Different configurations of lumen portions 300 can utilize the same threaded portion 200. Thus, the invention reduces the number of holes to be drilled into a patient's skull or the number of bolts to be screwed into and out of the same hole. Different configurations of lumen portion 300 are described below.

Referring to FIGS. 5 and 6, regardless of the type of mating connector 206, a fluid tight seal 306 is formed between inner surface 202 of threaded portion 200 and stem portion 302. In one embodiment, fluid tight seal 306 is formed from an o-ring 309 seated in a groove 308 in stem portion 302. Fluid tight seal 306 is required as pressures can build up under skull 102 and cranial fluid may leak through bolt 100. In one embodiment, o-ring 309 compresses against inner surface 202 and forms a barrier to prevent the passage of fluid.

Figure 7:
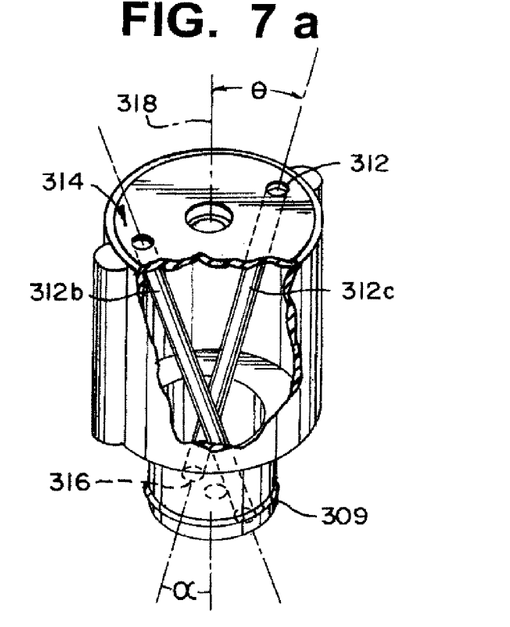
FIGS. 7a, 7b, and 7c are partially broken away perspective views of alternate embodiments of the lumen portion of the present invention.

Base portion 310 of lumen portion 300 is disposed on the end of stem portion 302 opposite skull 102. Base portion 310 extends outside and above threaded portion 200. At least two lumens 312 are disposed through stem portion 302 and base portion 310. Lumens 312 have a proximal end 314 opening outside skull 102 and a distal end 316 opening inside skull 102 (FIG. 7). One embodiment has three lumens, a drainage lumen 312a, and two sensor lumens 312b, 312c disposed offset from drainage lumen 312a. Another embodiment, illustrated in FIG. 7a includes one or both of proximal ends 314 and distal end 316 of lumens 312 diverging by an angle or angles from a centerline 318 of lumen portion 300. A further embodiment includes drainage lumen 312a disposed along centerline 318. Distal ends 316 of sensor lumens 312b, 312c may diverge by angle α from centerline 318. Proximal ends 314 can diverge from centerline 318 by an angle Θ. Disposing lumens 312 in a non-coaxial pattern allows the placement of multiple lumens at a distance further than a first lumen while minimizing the size of the bolt. For example, drainage lumen 312a is typically inserted to drain excess fluid from inside skull 102.

In preferred embodiments, illustrated in FIGS. 7b and 7c, lumens 312 are straight passageways and are angled in three-dimensions. FIG. 7b illustrates distal ends 316 are rotated in a plane in comparison with proximal ends 314. In one embodiment, all sensor lumens 312 are rotated by an angle or each sensor lumen can be rotated across a different angle (not illustrated). Another embodiment, illustrated in FIG. 7c, shows drainage lumen 312a along centerline 318 and sensor lumens 312b, 312c are rotated and divergent.

Figures 8, 9:
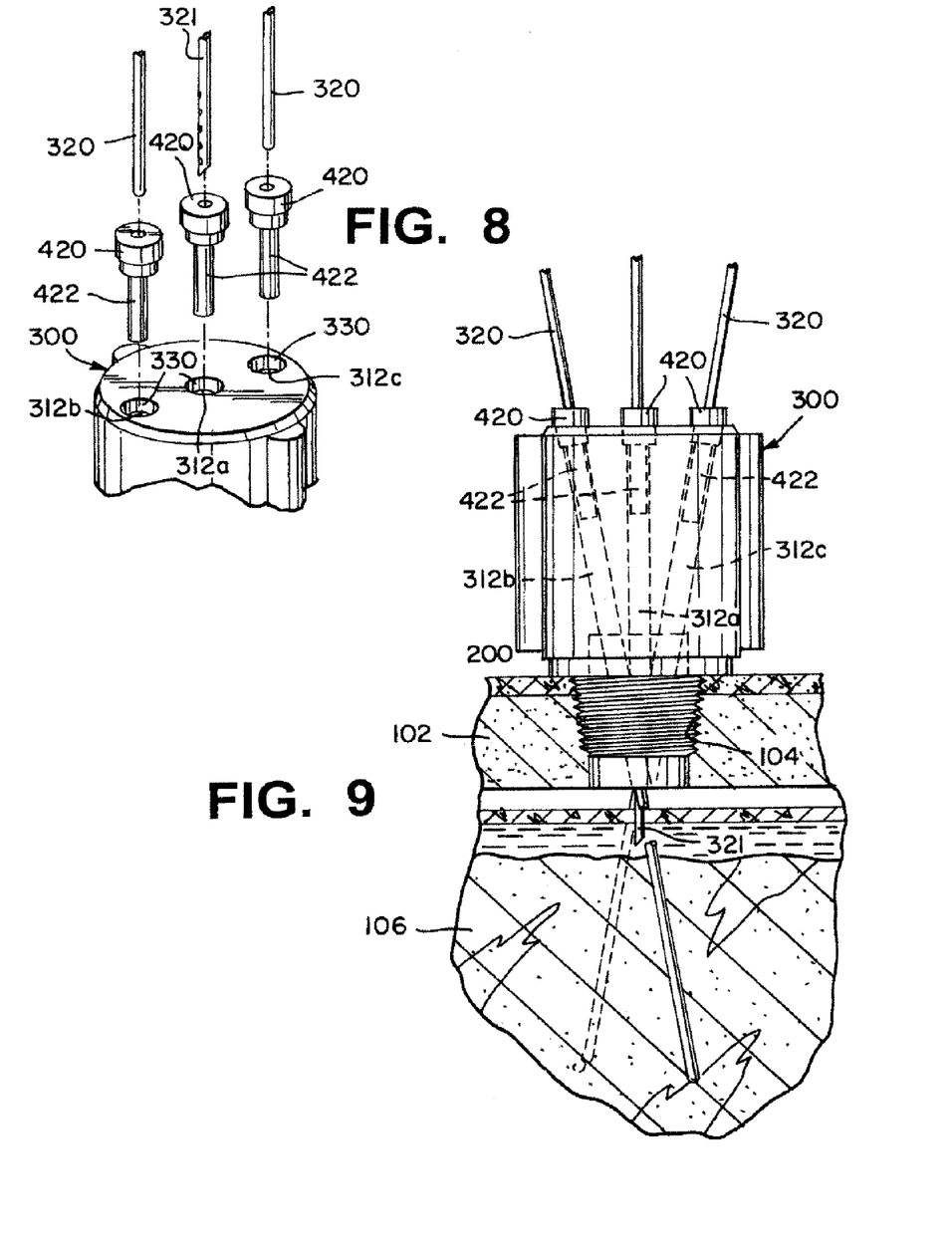
FIG. 8 is a perspective view of adaptors and sensors exploded from the top of the lumen portion of the present invention.
FIG. 9 is an elevation view of instruments inserted into the lumens of the present invention.

FIG. 8 illustrates the use of a touhy-borst adaptor 420 attached to a tube 422, preferably made of silicon. Lumen portion 300 has a recess 330 to fit the touhy-borst adaptor 420. FIG. 8 illustrates recess 330 for drainage lumen 312a and touhy-borst adaptor 420, which can also be used for sensor lumens 312b, 312c. Sensor 320 is passed through touhy-borst adaptor 420 and the touhy-borst adaptor 420 is used to lock sensor 320 in place.

As shown in FIG. 9, sensors 320 may be placed through sensor lumens 312b, 312c to take readings of the condition of brain 106. However, if sensors 320 are placed too close to a drainage catheter 321 inserted in drainage lumen 312a, sensors 320 will read the stresses and conditions caused by the drainage catheter and not the actual state of the brain 106. The same condition can occur if sensors 320 are placed in close proximity. The diverging angle α or Θ in FIG. 7a, causes a separation for the sensor 320 from the catheter 321 as they approach the brain.

Figures 10, 11:
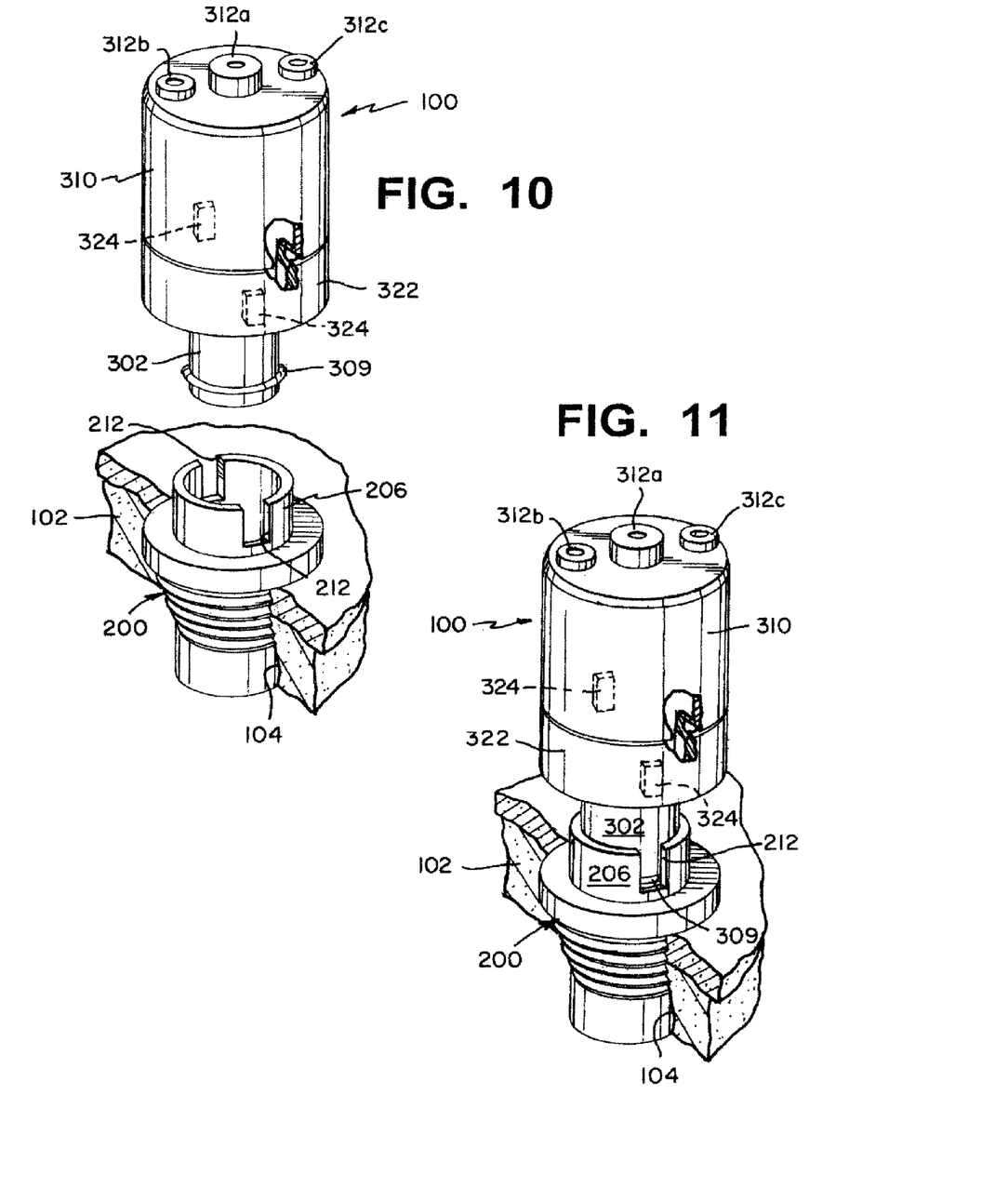
FIG. 10 is an exploded perspective view of a rotating embodiment of the present invention.
FIG. 11 is a perspective view of an embodiment of the present invention illustrating the rotating lumen portion engaging the threaded portion inserted into the brain of a patient.

Referring to FIGS. 10 and 11 and further to the above, cranial bolt 100 can include a floating collar 322 disposed between stem portion 302 and the base portion 310. Floating collar 322 allows lumen portion 300 to rotate relative to threaded portion 200. An additional embodiment allows base portion 310 to rotate relative to stem portion 302. Regardless of the embodiment, rotating base portion 310 allows for flexible placement of sensors 320 because lumens 312 are moved in relation to the rotational placement of threaded portion 200 on skull 102. Prior art bolts either fixed the position of the lumens once the bolt was screwed to the proper depth or required the entire bolt to be rotated if the placement of the sensors needed to be changed.

As further illustrated in FIG. 11, stem portion 302 is inserted into threaded portion 200 and floating collar 322 sits above, but does not engage mating connector 206. Base portion 310 can be rotated to position to place distal ends 316 so the sensors enter into the brain at the desired angle or position. Once base portion 310 is properly positioned, floating collar 322 can engage mating connector 206 to lock lumen portion 300 to threaded portion 200 and to prevent further rotation of base portion 310. This is achieved by having wing portions 324 on floating collar 322 engage in wing gaps 212 of threaded portion 200. Another embodiment locks floating collar 322 to mating connector 206 but continues to allow base portion 310 to rotate. Once base portion 310 is in the proper position, either floating collar 322 or base portion 310 is then further rotated to lock base position 310 to prevent further movement of the base portion.

The use of a floating collar 322 on cranial bolt 100 alleviates the need to move threaded portion 200 once placed to the proper depth in skull 102. Base portion 310 or lumen portion 300 can be rotated independent of threaded portion 200 without causing undue stress on skull 102.

Numbers of different configurations of lumen portions 300 can be designed for specific purposes. The configurations can vary by numbers of lumens 312 (e.g. 2, 3, or 4), configuration of the lumens (e.g. one central lumen and others offset or all the lumens on the perimeter), and the inclusion of floating collar 322. Also, while lumens 312 are shown as straight circular channels, they may curve along their length or have other changes in direction. Also, they may have other cross sections, e.g. square, triangular, etc.

Figure 12:
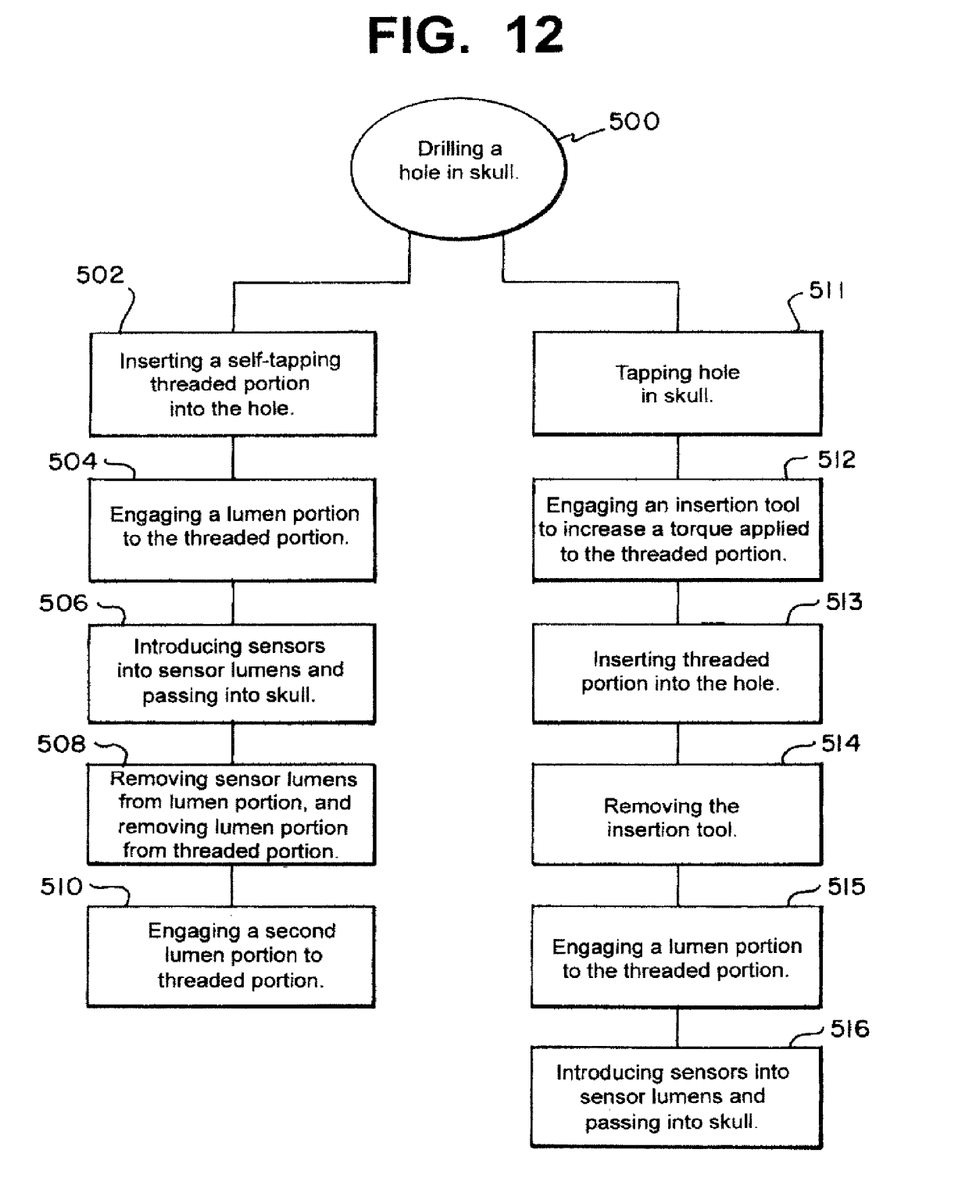
FIG. 12 is a flow chart illustrating a method of placing the cranial bolt.

FIG. 12 is a flow chart showing a method of securing cranial bolt 100 to skull 102 of a patient. The method includes drilling a hole 104 in the skull 102 (step 500) and inserting a self-tapping threaded portion 200 into the hole 104 (step 502). Threaded portion 200 includes mating connector 206 and an outer surface 208 having a plurality of threads 210 for engaging hole 104. Lumen portion 300 is engaged with threaded portion 200 (step 504). Lumen portion 300 forms a fluid tight seal 306 between inner surface 202 of threaded portion 200 and stem portion 302. The formation of the fluid tight seal 306 is described above. Once lumen portion 300 is engaged with threaded portion 200, sensors 320 can be introduced into sensor lumens 312 and passed into skull 102 (step 506).

Further methods include removing sensors 320 from lumen portion 300 and removing lumen portion 300 from threaded portion 200 (step 508), and engaging a second lumen portion (step 510). The second lumen portion can have a different configuration as described above (e.g. number, shape or placement of lumens 312).

An alternative method is shown in FIG. 12 in which, prior to the inserting step, an insertion tool 400 is engaged with threaded portion 200 (step 512) so as to increase the torque applied to the threaded portion during the insertion step. Threaded portion 200 is then inserted into the hole in the patient's skull (step 513. After the inserting step, the insertion tool is removed from the threaded portion 200 (step 514). Then continuing, the lumen portion 300 is engaged with the threaded portion (step 515) and sensors 320 are inserted through the lumens into the patient's skull (step 516). Other methods include tapping hole 104 prior to the insertion of threaded portion 200 (step 511) when a threaded portion is used which is not self-tapping.

Figure 13:
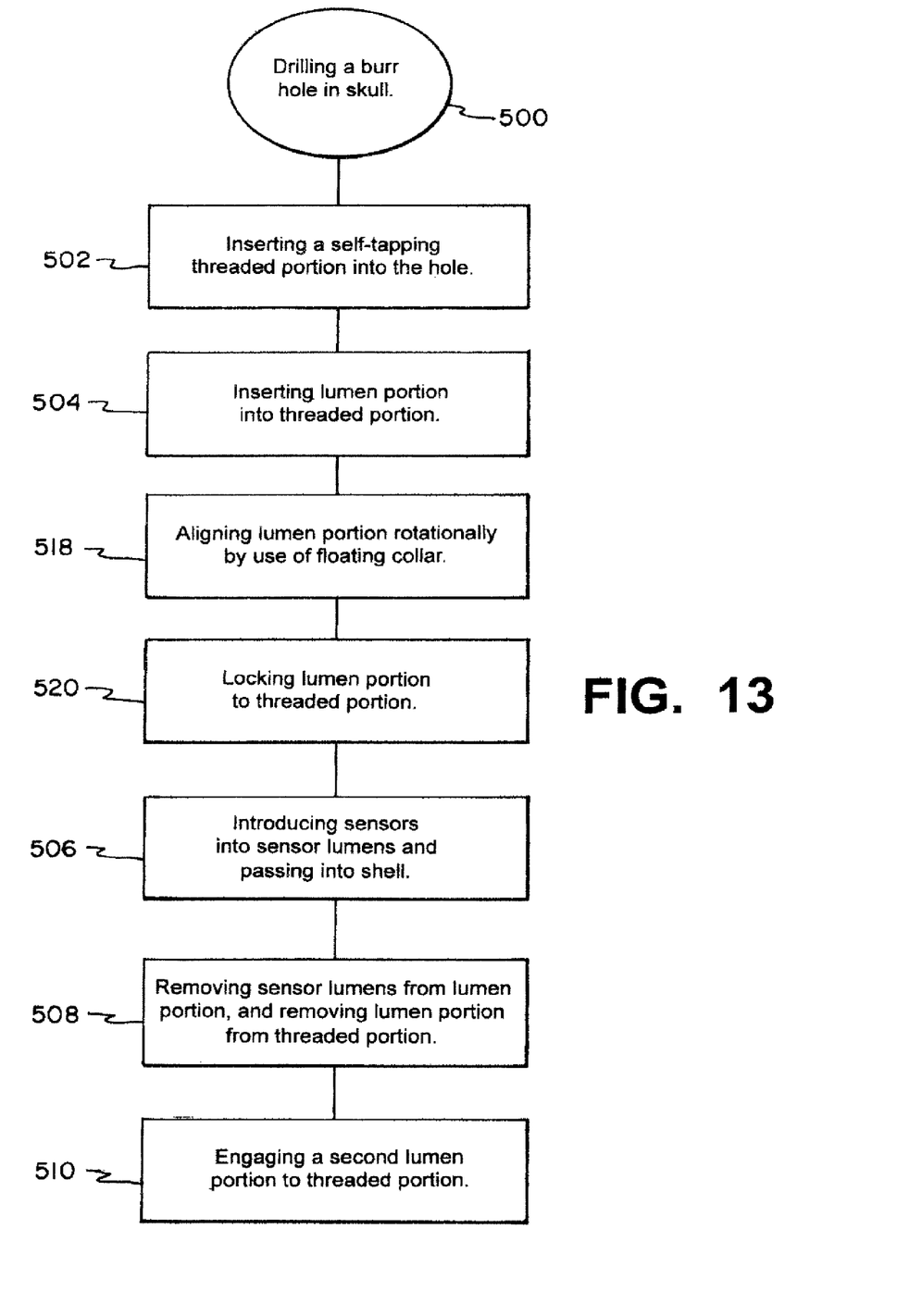
FIG. 13 is a flow chart illustrating an embodiment of the method of placing the cranial bolt.

FIG. 13 illustrates a preferred embodiment of a method of using cranial bolt 100 with a floating collar 322. As above, hole 104 is drilled in the skull 102 (step 500) and self-tapping threaded portion 200 is inserted into hole 104 (step 502). Lumen portion 300 can now be rotationally adjusted, as described above, by use of floating collar 322 (step 518). Once the lumen portion is properly aligned, lumen portion 300 can be fixed in place and locked to threaded portion 200 (step 520). Similar to above, once lumen portion 300 is engaged with threaded portion 200, sensors 320 can be introduced into sensor lumens 312 and passed into skull 102 (step 506). Further sensors 320 can be removed from lumen portion 300 and lumen portion 300 can be removed from threaded portion 200 (step 508). Finally a second lumen portion can be engaged with the threaded portion (step 510).

While there have been shown, described, and pointed out fundamental novel features of the invention as applied to a preferred embodiment thereof, it will be understood that various omissions, substitutions, and changes in the form and details of the devices illustrated, and in their operation, may be made by those skilled in the art without departing from the spirit and scope of the invention. For example, it is expressly intended that all combinations of those elements and/or steps which perform substantially the same function, in substantially the same way, to achieve the same results are within the scope of the invention. Substitutions of elements from one described embodiment to another are also fully intended and contemplated. It is also to be understood that the drawings are not necessarily drawn to scale, but that they are merely conceptual in nature. It is the intention, therefore, to be limited only as indicated by the scope of the claims appended hereto.

What is claimed is:

1. A method of securing a cranial bolt to a skull of a patient, the method comprising:

drilling a hole in the skull;

inserting a self-tapping threaded portion into the hole, wherein the threaded portion includes an inner surface forming a central passageway, a mating connector supported on the inner surface, and an outer surface having a plurality of threads for engaging the hole; and engaging a lumen portion to the threaded portion, wherein the lumen portion includes a stem part entering the central passageway and engaging the mating connector, a base part of the lumen portion disposed on one end of the stem part opposite the skull, and at least two lumens disposed through the stem part and the base part and wherein a proximal end of the at least two lumens opens outside the skull and a distal end of the at least two lumens opens inside the skull, wherein the at least two lumens extend through the stem part and the base part at an angle from the centerline of the lumen portion, the centerline of the lumen extends through the base part and the stem part.

2. The method of claim 1, wherein the engaging step is performed after the inserting step.

3. The method of claim 1, wherein the engaging step traps an o-ring between the inner surface of the threaded portion and the stem part to form a fluid tight seal.

4. The method of claim 1, wherein the engaging step is performed before the inserting step.

5. The method of claim 1, further comprising: removing the lumen portion; and engaging a second lumen portion.

6. The method of claim 1, wherein the lumen portion is rotatably engaged to the threaded portion.

7. The method of claim 1, further comprising: prior to the inserting step, engaging an insertion tool with the threaded portion to increase torque applied to the threaded portion during the insertion step; and after the inserting step, removing the insertion tool.

* * * * *